US008962327B2

(12) United States Patent
Yoon et al.

(10) Patent No.: US 8,962,327 B2
(45) Date of Patent: Feb. 24, 2015

(54) METHODS FOR CREATING COLOR VARIATION IN ANTHOCYANINS PRODUCED BY CELL CULTURE

(75) Inventors: Sung-Yong Yoon, Lake Oswego, OR (US); Helena V. Mathews, Portland, OR (US)

(73) Assignee: DianaPlantSciences, S.A.S., Rennes (FR)

( * ) Notice: Subject to any disclaimer, the term of this patent is extended or adjusted under 35 U.S.C. 154(b) by 65 days.

(21) Appl. No.: 13/260,667

(22) PCT Filed: May 4, 2009

(86) PCT No.: PCT/US2009/042730
§ 371 (c)(1),
(2), (4) Date: Sep. 27, 2011

(87) PCT Pub. No.: WO2010/114568
PCT Pub. Date: Oct. 7, 2010

(65) Prior Publication Data
US 2012/0034658 A1 Feb. 9, 2012

Related U.S. Application Data

(60) Provisional application No. 61/166,484, filed on Apr. 3, 2009.

(51) Int. Cl.
*C12N 5/04* (2006.01)
*A01H 4/00* (2006.01)
(52) U.S. Cl.
CPC ..... *C12N 5/04* (2013.01); *A01H 4/00* (2013.01)
USPC ........................................................ 435/430
(58) Field of Classification Search
USPC ........................................................ 435/430
See application file for complete search history.

(56) References Cited

U.S. PATENT DOCUMENTS

2008/0134356 A1* 6/2008 Rommens ..................... 800/278

OTHER PUBLICATIONS

Hale et al. Molybdenum Sequestration in *Brassica* Species. A role for Anthocyanins? Plant Physiology Aug. 2001 vol. 126, pp. 1391-1402.*
Yoshida et al. Ferric ions involved in the flower color development of the Himalayan blue poppy, *Meconopsis grandis*. Phytochemetry 67 (2006) 992-998.*
Rajendran et al. Anthocyanin Production in Callus Cultures of *Daucus carota* as influenced by nutrient stress and osmoticum. Biotechnology Letters vol. 14 No. 8 pp. 707-712. 1992.*
Mizukami et al. Anthocyanin production in callus cultures of roselle. Plant Cell Reports (1988) 7:553-556.*
Meyer et al. The in vitro production of an anthocyanin from callus cultures of *Oxalis linearis*. Plant Cell Tissue Culture 40:55-58. 1995.*

Luczkiewcz et al. Optimisation of the second phase of a two phase growth system for anthocyanin accumulation in callus cultures of *Rudbeckia hirta*. Plant Cell. Tissue and Organ Culture 65: 57-68, 2001.*
Sudha et al. Elicitation of anthocyanin production in callus cultures of *Daucus carota* and involvement of calcium channel modulators. Current Science vol. 84 No. 6 Mar. 2003.*
International Preliminary Report and Written Opinion dated Jun. 15, 2009, issued in PCT/US2009/42730, filed May 4, 2009.
International Search report dated Jun. 15, 2009, issued in PCT/US2009/42730, filed May 4, 2009.
Supplementary European Search Report dated Aug. 8, 2012, issued in Application No. EP 09 84 2835, filed May 4, 2009.
Werner E Glaβgen et al., *Regulation of Enzymes Involved in Anthocyanin Biosynthesis in Carrot Cell cultures in Response to Treatment with Ultraviolet Light and Fungal Elicitors*, Planta (Berlin), vol. 204, No. 4, Apr. 1998, XP002681448 pp. 490-498.
F. Bernard et al., *Comparison of Physiological and Biochemical Responds Between Two Varieties of Molybdenum Glycyrrhiza Blabra and Salicylic Acid*, Scientific Information Database, Rostaniha, XP002681449, 2008, pp. 1.
Mihoko Mori et al., *Structure of Anthocyanin from the Blue Petals of Phacelia Campanularia and its Blue Flower Color Development*, Phytochemistry, vol. 67, No. 6, Mar. 1, 2006, pp. 622-629.
V.R. Shenoy, *Anthocyanins—Perspective Food Colours*, Current Science, vol. 64, No. 8, Apr. 25, 1993, pp. 575-579.
G. Sudha et al., *Elicitation of Anthocyanin Production in Callus Cultures of Daucus carota and Involvement of Calcium Channel Modulators*, Current Science, vol. 84, No. 6, Mar. 25, 2003, pp. 775-779.
C. Curtin et al., *Manipulating Anthocyanin Composition in Vitis vinifera Suspension Cultures by Elicitation with Jasmonic Acid and Light irradiation*, Biotechnology Letters, vol. 25, 2003, pp. 1131-1135.
K. Sato et al., *Culturing Conditions Affecting the Production of Anthocyanin in Suspended Cell Cultures of Strawberry*, Plant Science, vol. 113, 1996, pp. 91-98.
M. Elhabiri et al., *Anthocyanin-aluminium and -gallium Complexes in Aqueous Solution*, J. Chem. Soc., Perkin Trans. vol. 2, 1997, pp. 355-362.
R. Brouillard et al., *The Copigmentation Reaction of Anthocyanins: A Microprobe for the Structural Study of Aqueous Solutions*, J. Am. Chem. Soc., vol. 111, 1989, pp. 2604-2610.
K. Hale et al., *Molybdenm Sequestration in Brassica Species. A Role for Anthocyanins?*, Plant Physiology., vol. 126, Aug. 2001, pp. 1391-1402.
M. M. Giusti et al., *Acylated Anthocyanins from Edible Sources and Their Applications in Food Systems*, Biochemical Engineering Journal, vol. 14, 2003, pp. 217-225.

(Continued)

*Primary Examiner* — Annette Para
(74) *Attorney, Agent, or Firm* — Workman Nydegger

(57) ABSTRACT

Disclosed are methods for obtaining blue anthocyanin pigments and compositions including such pigments. This blue anthocyanin is present at an acidic pH (where anthocyanins are most stable) and may be used as a natural color additive. The methods can include cultivating a plant callus from a plant capable of producing anthocyanin in which the callus is treated with a blue anthocyanin-generating agent at a concentration sufficient to generate callus with blue anthocyanin pigments. The method can also include recovering the blue anthocyanin pigments from the culture. In an example, the blue anthocyanin-generating agent is ammonium molybdate.

19 Claims, 3 Drawing Sheets

(56) References Cited

OTHER PUBLICATIONS

K. Takeda, *Blue Metal Complex Pigments Involved in Blue Flower Color*, Proc. Jpn. Acad. Ser. B., vol. 82, 2006, pp. 142-154.

V. S. Reddy et al., *Ultraviolet-B-Responsive Anthocyanin Production in a Rice Cultivar is Associated with a Specific Phase of Phenylalanine Ammonia Lyase Biosynthesis*, Plant Physiol., vol. 105, 1994, pp. 1059-1066.

A. H. Scragg, *Large-Scale Plant Cell Culture: Methods, Applications and Products*, Current Opinion in Biotechnology, vol. 3, 1992, pp. 105-109.

R. A. Taticek et al., *The Scale-Up of Plant Cell Culture: Engineering Considerations*, Plant Cell Tissue and Organ Culture, vol. 24, 1991, pp. 139-158.

Hooker et al., *Cultivation of Plant Cells in a Stirred Vessel: Effect of Impeller Design*, Biotechnology and Bioengineering, vol. 35, 1990, pp. 296-304.

Dong-Il Kim, et al., *A Hybird Bioreactor for High Density Cultivation of Plant Cell Suspensions*, Appl. Microbiology Biotechnol., vol. 34, 1991, pp. 726-729.

Kumi Yoshida et al., *Ferric Ions Involved in the Flower Color Development of the Himalayan Blue Poppy, Meconopsis Grandis*, Phytochemistry, vol. 67, 2006, pp. 992-998.

Simon Deroles, *Anthocyanin Biosynthesis in Plant Cell Cultures: A Potential Source of Natural Colourants*, © Springer+Business Media, LLC, 2009, Chapter 6, pp. 108-167.

Keiko Yonekura-Sakakibara et al., *Modification and Stabilization of Anthocyanins*, Springer Science+Business Media, LLC, 2009, Chapter 6, pp. 169-190.

Tadao Kondo et al., *Composition of Protocyanin, A Self-Assembled Supramolecular Pigment from the Blue Cornflower, Centaurea cyanus*, Angew. Chem. Int. Ed. Engl. vol. 33 No. 9, 1994, pp. 978-979.

\* cited by examiner

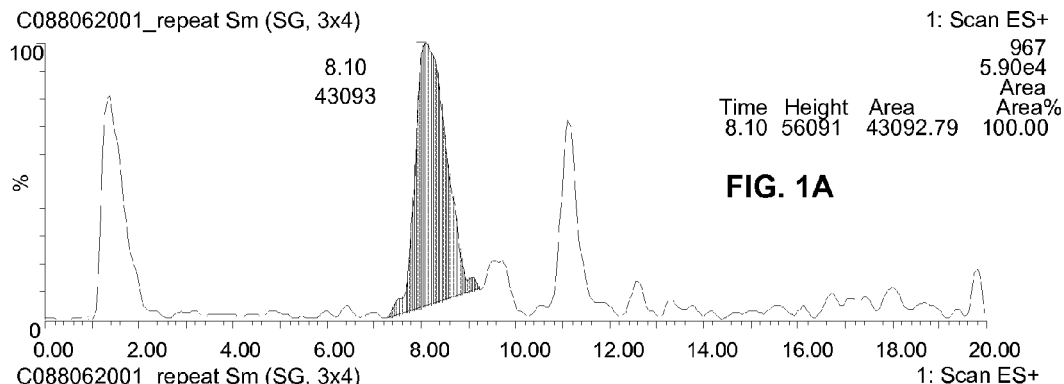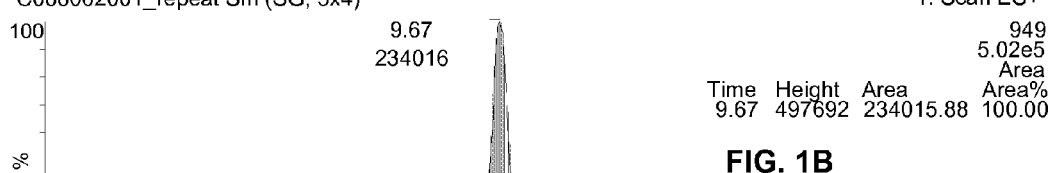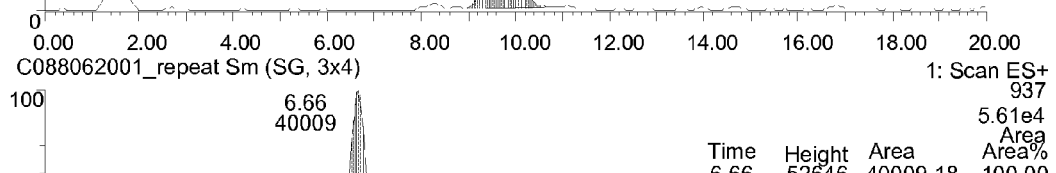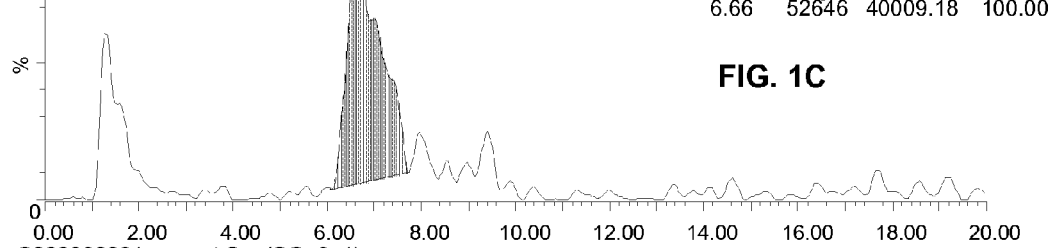
FIG. 1A: Hydrocyanidin-3-(ferulyl)-sophoroside-5-glucoside (MW: 967)
FIG. 1B: Cyanidin-3-(ferulyl)- sophoroside-5-glucoside (MW: 949)
FIG. 1C: Hydrocyanidin-3-(coumaroyl)- sophoroside-5-glucoside (MW: 937)
FIG. 1D: Cyanidin-3-(coumaroyl)- sophoroside-5-glucoside (MW: 919)

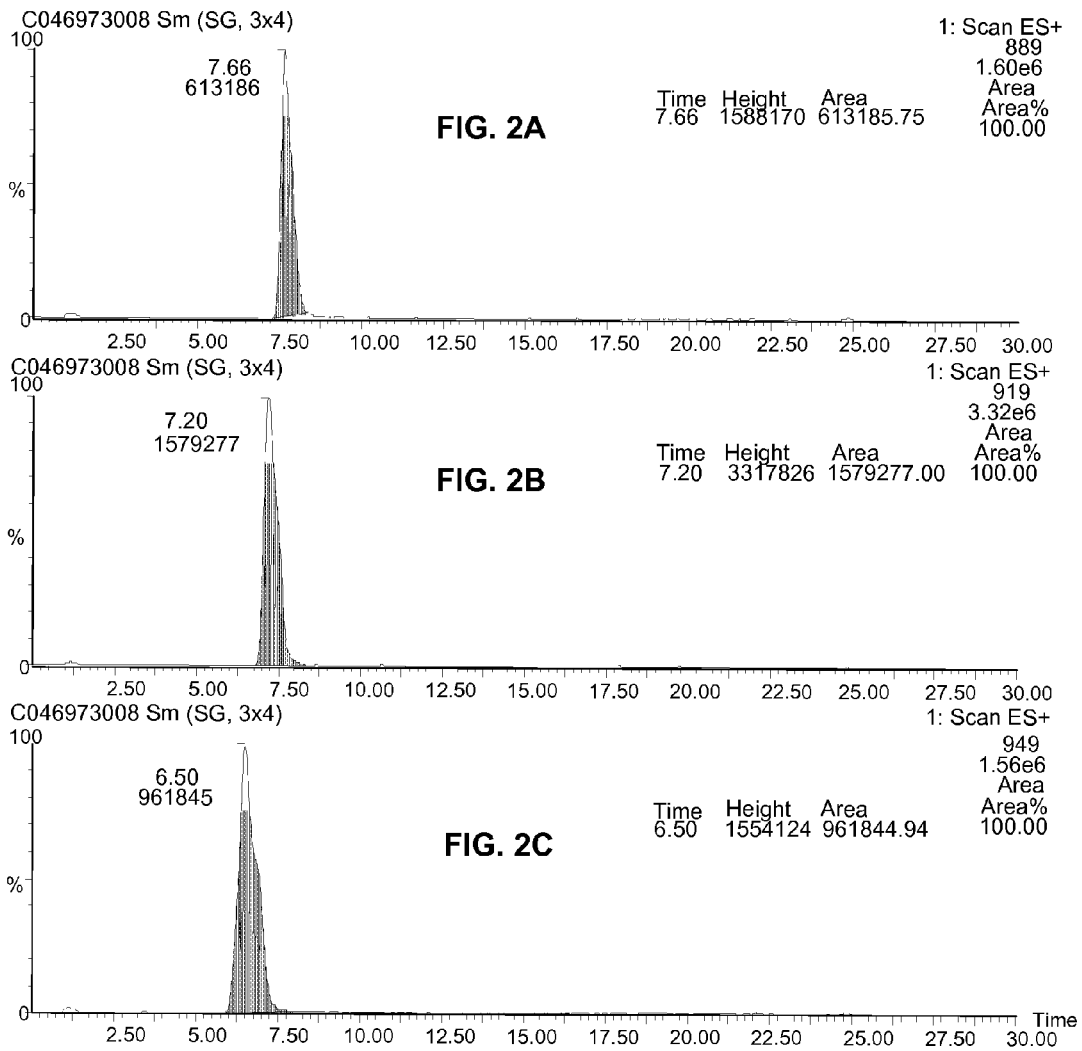
FIG. 2A: Cyanidin-3-(coumaroyl)-xylosylgucosyl-galactoside
FIG. 2B: Cyanidin-3-(ferulyl)-xylosylglucosyl-galactoside
FIG. 2C: Cyanidin-3-(synapyl)-xylosylglucosyl-galactoside

METHODS FOR CREATING COLOR VARIATION IN ANTHOCYANINS PRODUCED BY CELL CULTURE

CROSS-REFERENCE TO RELATED APPLICATION

This application claims the benefit of U.S. Provisional Application No. 61/166,484 filed on Apr. 3, 2009, which is incorporated herein by reference in its entirety.

FIELD OF THE DISCLOSURE

This disclosure relates to the field of plant cell culture and in particular, to the use of plant cell culture to produce or enhance the production of anthocyanins.

BACKGROUND

Synthetic food colorants are steadily being replaced by natural ones because of consumer preferences. Anthocyanins (polyphenolic pigments) are natural, water-soluble nontoxic pigments derived from fruits and vegetables, displaying a variety of colors from orange to blue. Because of their antioxidant properties, they may also have beneficial influence on human health (Shenoy, V. R., 1993, *Curr. Sci.* 64: 575-579). A drawback in the use of anthocyanins as food colorants is their low stability. In fact the color stability of anthocyanins depends on a combination of factors including chemical nature of anthocyanins, their concentration, pH, temperature and presence of complexing agents such as metal ions and phenolic compounds (Markakis, P., 1982, In: Markakis, P. (Ed.) *Anthocyanins as Food Colors*, Academic Press, New York, pp 163-180).

Common sources of anthocyanins used commercially as natural food colorants are grape skin extract, red cabbage, purple carrot, and elderberry. They are natural pH indicators, being red in acidic conditions where they are most stable and becoming bluer and more unstable as the pH increases. Thus, a source of stable natural blue color that can be used in the food and beverage industry remains to be identified.

Anthocyanins are produced by chopping or crushing the fruit or vegetable and subsequent infusion of water acidified with a common food acid. This extract is then concentrated by non-chemical separation techniques. Pigment extracts from plant sources generally contain mixtures of different anthocyanin molecules, which vary by their level of hydroxylation, methylation and acylation. These factors can vary in the source plant from year to year, and are influenced by weather and environmental factors. Thus, another challenge for the commercial production of anthocyanin pigments from plants is that harvest is often limited to once a year. This means a large volume of extract has to be prepared and stored for an extended period of time to supply the needs of the food industry throughout the year. Special storage conditions often have to be available due to the instability of anthocyanins.

SUMMARY OF THE DISCLOSURE

Disclosed herein are methods for obtaining blue anthocyanin pigments and compositions including such pigments. This blue anthocyanin is present at an acidic pH (where anthocyanins are most stable) and may be used as a natural color additive. Methods for producing blue anthocyanin include cultivating a plant callus from a plant capable of producing anthocyanin, in which method the callus is treated with a blue anthocyanin-generating agent at a concentration sufficient to generate callus with blue anthocyanin pigments. The method can also include recovering the blue anthocyanin pigments from the culture. In an example, the blue anthocyanin-generating agent is ammonium molybdate. In another example, the blue anthocyanin-generating agent is ferric pyrophosphate or ferric citrate.

In an embodiment, a method for producing blue anthocyanin pigments includes cultivating a plant callus from a plant (such as a callus obtained from a cotyledon, root, hypocotyl, shoot tip, stem, leaf, or epidermal peel) in a liquid medium to obtain a suspension cell culture capable of producing at least one of red or purple anthocyanins. The method can also include contacting the plant suspension cell culture with a blue anthocyanin-generating agent to produce blue anthocyanin pigments, wherein the liquid medium comprises the blue anthocyanin-generating agent at a concentration sufficient to generate callus with blue anthocyanin pigments. The method can further include recovering the blue anthocyanin pigments from the cell culture. In a specific example, cultivating a plant callus includes inducing the formation of the plant callus from a tissue explant of a plant capable of producing at least one of red or purple anthocyanin through in vitro culture in a suitable nutrient medium (e.g., a solid medium).

A blue anthocyanin-generating agent can be at least one of ammonium molybdate, $Fe^{3+}$ salts, $Al^{3+}$ salts, $Mn^{2+}$ salts, $Zn^{2+}$ salts, $Ni^{2+}$ salts, $Cu^{2+}$ salts, $Co^{2+}$ salts, $K^+$ salts or a combination thereof. In one particular embodiment, a blue anthocyanin-generating agent is ammonium molybdate (such as at a concentration of 1 mg/L to 150 mg/L) either alone or in combination with other metal ions. In another example, the blue anthocyanin-generating agent is ferric pyrophosphate or ferric citrate.

The foregoing and other features will become more apparent from the following detailed description of several embodiments, which proceeds with reference to the accompanying figures.

BRIEF DESCRIPTION OF THE FIGURES

FIGS. 1A-AD are histograms of LC/MS analysis of an anthocyanin composition of cabbage callus cells.

FIGS. 2A-2C are histograms of LC/MS analysis of an anthocyanin composition of carrot suspension cells.

DETAILED DESCRIPTION

I. Introduction

Figure 3:
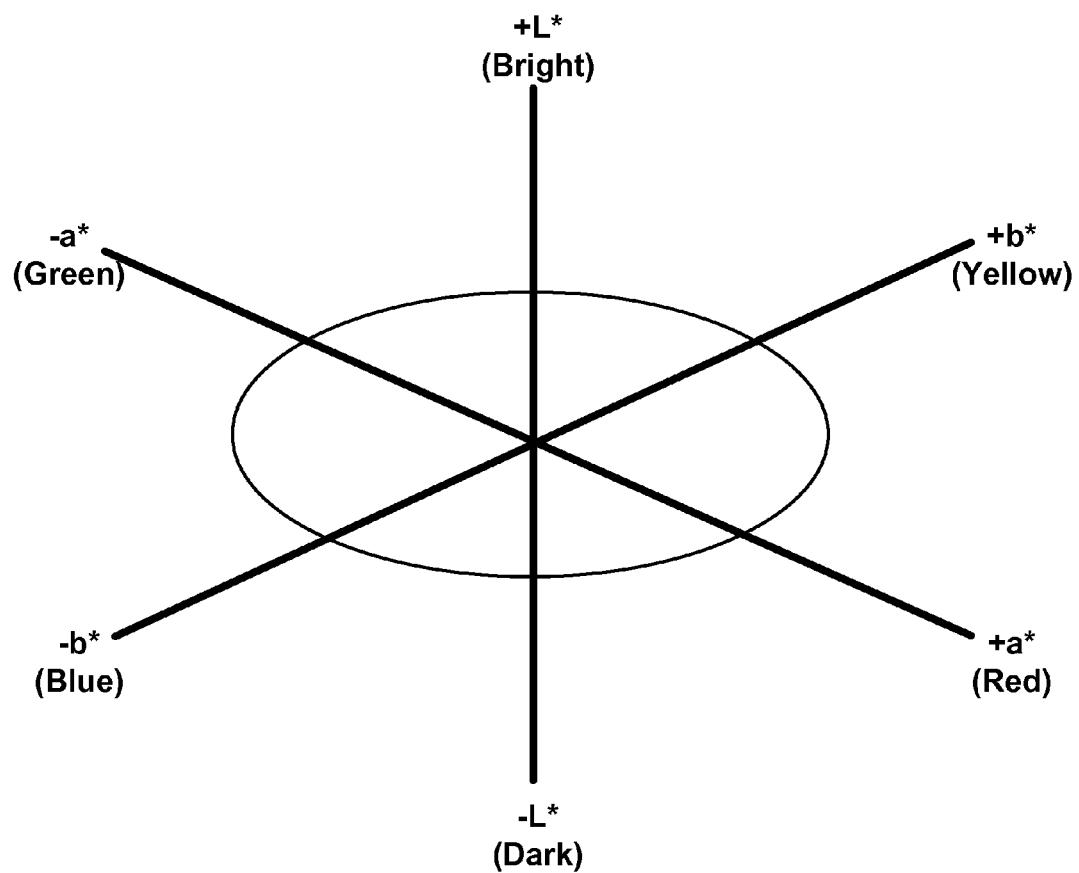
FIG. 3 is an a*, b* chromaticity diagram in which a* and b* indicate color directions: +a* is the red direction, −a* is the green direction, +b* is the yellow direction, and −b* is the blue direction. The center is achromatic; as the a* and b* values increase and the point moves out from the center, the saturation of the color increases.

A viable cell culture system for the production of anthocyanins has several potential advantages, including facilitating selective production of stable bioactive anthocyanin molecules and circumventing problems of uncertain, variable or seasonal supply. This involves development of a tissue culture system from a source plant and growing large scale plant suspension cultures similar to microbial fermentation systems. Growing plant cells in culture provides a highly controlled environment where nutrients can be manipulated to enhance cell growth and/or anthocyanin productivity. Though there is no commercial process for the production of anthocyanins from plant cell culture, various groups have developed cell cultures from grape and carrot that produce anthocyanins (Curtin et al., 2003, *Biotech. Letters* 25: 1131-1135; Sudha and Ravishankar, 2003, *Curr. Sci.* 84: 775-779). Since anthocyanin extracts are only stable at acidic pH, the extracts derived from these cell cultures are not blue. However, cell cultures are amenable to treatments such as chemical or physical elicitation to increase secondary metabolite production. For example, anthocyanin production by plant cell cultures can be increased by exposing the cultures to various light conditions (Sato et al., 1996, *Plant Sci.*, 113: 91-98). Similarly, we have developed and described here processes for treating anthocyanin producing cell cultures with a color modulator to produce blue color in resultant extracts at acidic pH.

Metallic complexation of anthocyanins is a process strong enough to induce impressive color changes going from pale-red to deep-purple (Elhabiri et al., 1997, *J. Chem. Soc., Perkin Trans.* 2: 355-362). Small highly charged metal ions such as $Al^{3+}$ and $Mg^{2+}$ have been reported to possibly strengthen the pigment-copigment interaction leading to hyperchromic and bathochromic shifts. In particular, it has been proposed that the blue color displayed by some flowers is the result of pigment-copigment-metal ion assemblies (Brouillard et al., 1989, *J. Am. Chem. Soc.*, 111: 2604-2610).

When Indian mustard (*Brassica juncea*) seedlings were grown on agar medium containing different concentrations of ammonium molybdate, they showed blue coloration, especially at the base of the hypocotyls and around the petioles (Hale et al., 2001, *Plant Physiol.*, 126: 1391-1402). Cross sections of the molybdenum-treated seedlings showed the blue color was present in a crystal-like form, localized predominantly in the epidermal and subepidermal tissues. Molybdenum was accumulated primarily in the epidermal cells of the hypocotyls, correlating with the location of the blue compound. Further, most of the molybdenum was located in vacuoles. The blue color was extracted from ground tissue and was found to be soluble in water and determined to be anthocyanins. Thus, it has been shown that in the presence of molybdenum, anthocyanins in acidic extracts can turn blue.

In the present study addition of molybdenum as ammonium molybdate to the tissue culture medium led to the formation of blue anthocyanins. However, unlike in the above study, the blue color pigment was not limited to specific cells or the periphery of the callus. With the disclosed methods, all cells in the callus showed blue color pigment (as demonstrated in the Examples below). This was also the case with the suspension cells. Additionally, the use of ammonium molybdate for the production of blue colored anthocyanins in tissue and cell culture has not been previously described.

II. Overview of Several Embodiments

Disclosed herein are methods for obtaining blue anthocyanin pigments and compositions including such pigments. In one embodiment, methods for providing blue anthocyanin can include cultivating a plant callus from a plant (such as a callus obtained from a cotyledon, root, hypocotyl, shoot tip, stem, leaf, or epidermal peel) in a liquid medium to obtain a suspension cell culture capable of producing anthocyanin, in which method the liquid medium is treated with a blue anthocyanin-generating agent at a concentration sufficient to generate callus with blue anthocyanin pigments. In some particular examples, blue anthocyanin pigments are present at a pH of 1 to 5. The method can also include recovering the blue anthocyanin pigments from the culture. In some examples, cultivating a plant callus includes inducing the formation of the plant callus from a tissue explant of a plant capable of producing blue anthocyanin through in vitro culture in a suitable nutrient medium. For example, the nutrient medium used in the induction of the formation of the plant callus can include a solid medium.

In an embodiment, a method for producing blue anthocyanin pigments includes cultivating a plant callus from a plant (such as a callus obtained from a cotyledon, root, hypocotyl, shoot tip, stem, leaf, or epidermal peel) in a liquid medium to obtain a suspension cell culture capable of producing at least one of red or purple anthocyanins. The method can also include contacting the plant suspension cell culture with a blue anthocyanin-generating agent to produce blue anthocyanin pigments, wherein the liquid medium comprises the blue anthocyanin-generating agent at a concentration sufficient to generate callus with blue anthocyanin pigments. The method can further include recovering the blue anthocyanin pigments from the cell culture. In a specific example, cultivating a plant callus includes inducing the formation of the plant callus from a tissue explant of a plant capable of producing at least one of red or purple anthocyanin through in vitro culture in a suitable nutrient medium (e.g., a solid medium). A blue anthocyanin-generating agent can be at least one of ammonium molybdate, $Fe^{3+}$ salts, $Al^{3+}$ salts, $Mn^{2+}$ salts, $Zn^{2+}$ salts, $Ni^{2+}$ salts, $Cu^{2+}$ salts, $Co^{2+}$ salts, $K^+$ salts or a combination thereof. In one particular embodiment, a blue anthocyanin-generating agent is ammonium molybdate (such as at a concentration of 1 mg/L to 150 mg/L) either alone or in combination with other metal ions. In another example, the blue anthocyanin-generating agent is one or more $Fe^{3+}$ salts, ferric pyrophosphate, ferric citrate or combination thereof.

A blue anthocyanin-generating agent can be added at any time during the cell culture process, such as the time the culture is initiated or at the time of cell harvest or any time in between. Blue anthocyanin is then extracted from cells that are harvested from the cell culture.

In yet another embodiment, the blue anthocyanin-generating agent can also be added to the anthocyanin extract derived from cells grown on medium lacking the blue anthocyanin-generating agent.

In some embodiments, the plant is of the genus *Brassica* or *Daucus*. For example, the plant can belong to the species *Brassica oleraceae* or *Daucus carota*.

III. Abbreviations and Terms

A. Abbreviations
B5: Gamborg's B5 salts
BA: benzyl adenine
2,4-D: 2,4-dichlorophenoxyacetic acid
FD&C: Food, Drug & Cosmetic act
GA: gibberellic acid
HPLC: high pressure liquid chromatography
IAA: indole 3-Acetic Acid
LC/MS: liquid chromatography-mass spectrometry
MS: Murashige & Skoog
NAA: 1-Naphthaleneacetic Acid
NN: Nitch & Nitch
PCV: packed cell volume
RPM: revolutions per minute
UV: ultraviolet
2iP: 6-γ,γ-Dimethylallylaminopurine B. Terms
In order to facilitate review of the various embodiments of the disclosure, the following explanations of specific terms are provided:

Ammonium molybdate: A compound with the chemical formula of $(NH_4)_6MO_7O_{24} \cdot 4H_2O$ and a molecular weight of 1235.86. Ammonium molybdate is also known as molybdic acid hexammonium salt tetrahydrate, ammonium molybdate tetrahydrate, ammonium heptamolybdate tetrahydrate or molybdic acid. In an example, ammonium molybdate is a blue-anthocyanin generating agent. In a particular example, ammonium molybdate at a concentration ranging from greater than 0 mg/L to approximately 150 mg/L is employed to generate blue anthocyanin pigments that can be extracted and utilized as a natural color additive. For example, the concentration of ammonium molybdate is at least 3 mg/L, at least 6 mg/L, at least 9 mg/L, at least 30 mg/L, at least 60 mg/L, at least 120 mg/L, or at least 150 mg/L.

Anthocyanins: A group of water-soluble flavonoids that impart pink/red to purple color to leaves and other organs of plants. Common anthocyanins include derivatives of cyanidin, delphinidin, malvidin and pelargonidin. In an example, anthocyanin pigments are pigments formed after addition of ammonium molybdate with an absorption spectra at 520 nm.

Blue-anthocyanin generating agents: Metal ions that change the color of anthocyanins to blue. Some highly charged metal ions, such as $Al^{3+}$ and $Mg^{2+}$, are able to form complexes with pigments and copigments, resulting in a standard blue color. In an example, the blue-anthocyanin generating agent is a $Fe^{3+}$, $Mg^{2+}$, $Mo$, $Ca^{2+}$, $Al^{3+}$, $Mn^{2+}$, $Zn^{2+}$, $Ni^{2+}$, $Cu^{2+}$, $Co^{2+}$, $Na^+$ or $K^+$ salt or combination or mixture thereof. In another example, a blue-anthocyanin generating agent is ammonium molybdate. In yet another example, the blue anthocyanin-generating agent is ferric pyrophosphate or ferric citrate.

The term "blue" may refer to any of a number of similar colors, such as any color ranging from navy blue to cyan. The sensation of blue is made by light having a spectrum dominated by energy in the wavelength range of about 440-490 nm. In an example, the color blue is defined by the Royal Horticultural Society Color Chart (2001) and includes color number N92-121

Callus: A mass of undifferentiated cells. A plant cell callus consists of somatic undifferentiated cells from a subject plant, such as an adult subject plant or a plant part including plant embryo. In an example, a callus of red cabbage is cultured on a solid medium and treated with agents capable of altering the color variation in anthocyanins produced by the callus.

Concentration sufficient to: A phrase used to describe an amount of an agent that alone, or together with one or more additional agents, induces the desired response or effect. In an example, the phrase is used to describe an amount of a blue-anthocyanin generating agent ($Fe^{3+}$, $Mg^{2+}$, $Mo$, $Ca^{2+}$, $Al^{3+}$, $Mn^{2+}$, $Zn^{2+}$, $Ni^{2+}$, $Cu^{2+}$, $Co^{2+}$, $Na^+$ or $K^+$ salt, ammonium molybdate, ferric pyrophosphate, ferric citrate or combination or mixture thereof) generates blue-anthocyanins.

pH: A measure of the acidity or alkalinity of a solution. An aqueous solution at 25° C. with a pH less than seven is acidic, while a solution with a pH greater than seven is considered basic (alkaline). In an example, an acidic pH is less than five, such as between one and three.

Plant cell: Any cell derived from a plant, including cells from undifferentiated tissue (e.g., callus) as well as plant seeds, pollen, propagules and embryos. Plant cells can be obtained from any plant organ or tissue and cultures prepared therefrom.

Plant part: Any plant organ or tissue, including, without limitation, seeds, embryos, meristematic regions, callus tissue, leaves, roots, shoots, stems, gametophytes, sporophytes, pollen, and microspores.

Purple carrot: The purple carrot (*Daucus carota*) is a cultivar of carrot. Carrot cultivars are generally grouped into two groups, eastern and western. Eastern carrots were domesticated in Central Asia, probably in modern-day Afghanistan in the 10th century, or possibly earlier. Specimens of the eastern carrot that survive to the present day are commonly purple or yellow, and often have branched roots. The purple color common in these carrots comes from anthocyanin pigments.

Red cabbage: The Red Cabbage (*Brassica oleracea* var. *capitata* f. *rubra*) is a variety of cabbage, also known as Red Kraut or Blue Kraut after preparation (e.g., the blue color is formed after cooking).

Suspension culture: The growth of cells separate from the organism. This is typically facilitated via use of a liquid medium. Suspension culture can refer to the growth of cells in liquid nutrient media.

Tissue culture: Tissue culture commonly refers to the culture of cells and tissues on solid nutrient media.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A, or B, or A and B.

It is further to be understood that all base sizes or amino acid sizes, and all molecular weight or molecular mass values, given for nucleic acids or polypeptides or other molecules are approximate, and are provided for descriptive purposes, unless otherwise indicated. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., DiCosmo, F. and Misawa, M. (Eds.) *Plant Cell Culture Secondary Metabolism*, 1996, CRC Press, Boca Raton, 232 pp; Payne, G. F., Bringi, V., Prince, C. L., and Shuler, M. L. *Plant cell and tissue culture in liquid systems*, 1992, John Wiley & Sons, Inc, New York, 346 pp; Gamborg, O. L. and Phillips, G. C. (Eds.). *Plant cell, tissue and organ culture: Fundamental methods*, 1995, Springer-Verlag Berlin Heidelberg, 307 pp; Fu, T-J, Singh, G., and Curtis, W. R. (Eds.). *Plant cell and tissue culture for the production of food ingredients*, Kluwer Academic/Plenum Publishers, New York, 290 pp, each of which is specifically incorporated herein by reference in its entirety.

IV. Methods of Producing or Enhancing Blue Anthocyanin Pigments

Methods of producing or enhancing blue anthocyanin pigments are disclosed herein. In an embodiment, the methods include cultivating a plant callus from a plant capable of producing anthocyanin in which the callus is treated with a blue anthocyanin-generating agent at a concentration sufficient to generate callus with blue anthocyanin pigments. The method can also include recovering the blue anthocyanin pigments from the culture.

In an example, the callus producing the blue anthocyanin can be used to raise suspension cultures of cells producing blue anthocyanins and such cultures can be used to extract blue anthocyanins. For example, the callus producing anthocyanins that are red or purple can be used to raise suspension cultures. Such anthocyanin-producing suspension cultures can be treated with a blue anthocyanin-generating agent at a concentration sufficient to generate callus with blue anthocyanin pigments. The method can also include recovering the blue anthocyanin pigments from the culture.

The blue anthocyanin-generating agent can be added at any time during the cell culture process such as the time the culture is initiated or at the time of cell harvest or any time in between and blue anthocyanin extracted from the cells that are harvested. The blue anthocyanin-generating agent can also be added to the anthocyanin extract derived from cells grown on medium lacking the blue anthocyanin-generating agent.

Plants Capable of Producing Anthocyanin.

Anthocyanins include a diverse group of intensely colored pigments responsible for colors ranging from orange, red purple and blue colors of many fruits, vegetables, flowers, leaves, roots and other plant storage organs. A number of food plants are used as sources of anthocyanin-based colorants, such as highly pigmented fruits including extracts of red grapes and its by-products (Markakis, 1992, In: Markakis, P. (Ed.) *Anthocyanis as Food Colors*, Academic Press, New York, Chapter 6), cranberry press cake (Clydesdale et al., 1979, *J. Food Prod.*, 42: 204-207), blueberries (Francis, 1985, *J. Food. Sci.*, 50: 754-756), black chokeberries (Kramer-Schafhalter et al., 1996, *Proceedings of the Second International Symposium on Natural Colorants INF/COL II*, The Hereld Organization, Acapulco, Mexico), elderberries (Bronnun-Hansen et al., 1986, *J. Food Technol.*, 21: 605-614), *Hibiscus calyces* (Pouget et al., 1990, *Lebensm. —Wiss. U. —Technol.*, 23: 103-105), and black currants (Rosa, 1973, *PR Inst. Lab. Badaw. Przem. Spozyw.*, 23: 269-300). Examples of vegetable sources of anthocyanins that may impart desirable color and stability include radishes, red potatoes, red cabbage, black carrots, and purple sweet potatoes (Giusti and Worlstad, 2003, *Biochem. Eng. J.*, 14: 217-225). In particular examples, red cabbage or purple carrot is employed to generate cell cultures from which blue anthocyanin pigments can be extracted.

Blue Anthocyanin-Generating Agents.

Metal complexes of anthocyanins are known to be involved in the true blue flower color (Takeda, 2006, *Proc. Jpn. Acad. Ser. B.*, 82: 142-154). The blue pigment of corn flower, named protocyanin, was revealed by X-ray structure analysis to be a tetra-metal ($Fe^{3+}$, $Mg^{2+}$, $2Ca^{2+}$) nuclear complex of twelve molecules of anthocyanin and flavone glycoside, involving copigmentation and intermolecular hydrophobic association. The elucidation of the molecular structures of anthocyanins in blue flowers demonstrated that the true blue color is developed by the metal complex pigments. The blue color of the blue flowers of *Salvia patens* and the blue sepals of *Hydrangea macrophylla* is also developed by metal complex pigments. Participation of the bivalent metal ions, $Mg^{2+}$ and $Ca^{2+}$, as well as trivalent ions, $Fe^{3+}$ and $Al^{3+}$, in the formation of blue color in those flowers is now well established. Other metal ions have also been shown to produce blue anthocyanins such as $Mn^{2+}$, $Co^{2+}$, $Ni^{2+}$, $Zn^{2+}$ and $Cd^{2+}$.

In an example, the blue-anthocyanin generating agent is a $Fe^{3+}$, $Mg^{2+}$, Mo, $Ca^{2+}$, $Al^{3+}$, $Mn^{2+}$, $Zn^{2+}$, $Ni^{2+}$, $Cu^{2+}$, $Co^{2+}$, $Na^+$ or $K^+$ salt, ferric pyrophosphate, ferric citrate or combination thereof. In another example, a blue-anthocyanin generating agent is molybdenum. In some examples, a blue-anthocyanin generating agent includes ammonium molybdate and at least one of $Fe^{3+}$ salt, ferric pyrophosphate or ferric citrate. In a particular example, ammonium molybdate is provided at a concentration ranging from greater than 0 mg/L to approximately 150 mg/L. For example, the concentration of ammonium molybdate is at least 3 mg/L, at least 6 mg/L, at least 9 mg/L, at least 30 mg/L, at least 60 mg/L, at least 120 mg/L, or at least 150 mg/L.

Culture Conditions Utilized to Generate Blue Anthocyanins.

In an example, plant callus and/or suspension cultures are employed to generate blue anthocyanins. Plant callus can be obtained from an appropriate plant using art recognized techniques. The plant tissue can be from a variety of sources, including a cotyledon, root, hypocotyl, shoot tip, stem, leaf, or epidermal peel. The callus can be induced from a tissue explant of a plant capable of producing blue anthocyanin through in vitro culture in a suitable nutrient medium. For example, the nutrient medium used in the induction step of the formation of the callus comprises a solid medium.

Callus and suspension cultures from plants producing anthocyanin pigments can be established by protocols known in the art. Exemplary protocols are provided in the Examples below. Briefly, although the following specifics may be varied by those skilled in the art, in a representative method, initiation of an anthocyanin-producing cell culture is achieved by setting up callus and suspension cultures from stable, continuous tissue cultures.

Callus and suspensions cells may produce anthocyanins naturally. However, at times, though the host plant produces anthocyanins, the callus and/or suspension cultures may not. In such instances, the cultures can be induced to produce anthocyanins using light irradiation, especially ultra violet (UV)-B light which is an elicitor of anthocyanin biosynthesis (Reddy et al., 1994, *Plant Physiol.* 105: 1059-1066). In other instances, such as with red cabbage, seedlings do not produce anthocyanins naturally. When parts of the seedlings are used to initiate callus cultures it is possible to induce the seedlings to produce anthocyanin pigments by exposing the germinating seeds to light such as UV-B. The anthocyanin-producing seedlings then can be used to initiate callus cultures.

Suspension cultures can be raised from the callus cultures and maintained in fresh suspension medium (as detailed in the Examples below). Pigmented suspension cultures can be established by aseptically transferring a known mass of cells expressed as packed cell volume (PCV) to fresh medium on a regular schedule, typically at 7-14 days intervals.

In accordance with the present disclosure, the production of blue pigmented anthocyanins from such cultures is achieved by the addition of a metal salt, such as ammonium molybdate, ferric pyrophosphate or ferric citrate. Such salts can be added to any of the nutrient media used to initiate or maintain callus and suspension cultures. In one aspect of this disclosure, initially suspension cultures are raised from unpigmented calli and do not produce anthocyanins. These suspensions can be plated on solid media that contain agents such as ammonium molybdate that produce blue anthocyanins and calli and allowed to develop from the plated suspension cells. Under these conditions, a portion of the developing callus has the ability to produce blue colored anthocyanins (e.g., each callus may have a mixture of blue and white cells and the blue cells are selected). When these calli are removed from the media containing the blue pigment producing agent and placed on media without such agents, the new developing calli will then produce the normal red to purple colored anthocyanins.

In another aspect of the disclosure, the blue anthocyanin forming agent can be added at any stage of the suspension culture growth cycle. In an example, the blue-anthocyanin generating agent is a $Fe^{3+}$, $Mg^{2+}$, $Mo$, $Ca^{2+}$, $Al^{3+}$, $Mn^{2+}$, $Zn^{2+}$, $Ni^{2+}$, $Cu^{2+}$, $Co^{2+}$, $Na^+$ or $K^+$ salt, ferric pyrophosphate, ferric citrate or combination thereof. In another example, a blue-anthocyanin generating agent is molybdenum. In a particular example, ammonium molybdate is provided at a concentration ranging from greater than 0 mg/L to approximately 150 mg/L. For example, the concentration of ammonium molybdate is at least 3 mg/L, at least 6 mg/L, at least 9 mg/L, at least 30 mg/L, at least 60 mg/L, at least 120 mg/L, or at least 150 mg/L. In one instance, the ammonium molybdate is added at the time of subculture. Blue color is detected in the culture as early as one hour after treatment. In another instance, the agent such as ammonium molybdate is added up to twenty four hours prior to harvest or recovery of the suspension cells, and blue color anthocyanins are extracted from the harvested or recovered cells. In a further instance, the blue color forming agent such as ammonium molybdate is added at the time of cell harvest and the blue colored anthocyanins extracted from the cells. It is also possible to add the blue color forming agent such as ammonium molybdate after the anthocyanins are extracted from the cells. In this instance, the initial anthocyanin extract is red or purple and turns blue after the addition of an appropriate amount of the blue color forming agent such as ammonium molybdate.

V. Recovery or Harvesting of Blue-Anthocyanin Pigments

Blue colored anthocyanins are recovered or extracted from cell cultures in ways similar to the methods known in the art for extraction of any other anthocyanins. For example, in a representative embodiment, cells are homogenized and extracted with acidified water (0.05% sulfuric acid, pH 3.0). Modifications to the solvent used for extraction include the addition of ethanol or methanol (up to 50% volume/volume) and the use of acetic acid or any other food grade acid to acidify the solvent (instead of sulfuric acid). The cells may be frozen prior to homogenization if storage is required. For example, cells can be frozen in liquid nitrogen and stored at −80° C.

In one example, the cell suspension cultures are homogenized before removing the spent medium, and the resultant homogenate is filtered. The filtered homogenized cell mass can then be extracted with solvent to remove anthocyanins. In another example, the cell culture is filtered to remove the spent medium and solvent added to the remaining cell mass, then the cells are homogenized in the presence of solvent. In an additional example, spent medium is decanted, the solvent is added to the remaining cell mass, cells are homogenized, and anthocyanins extracted. In all of the aforementioned examples, anthocyanin extraction with solvent may be repeated several times to extract as much anthocyanins as possible from the cell mass. In a particular example, such as when the blue color-forming agents such as ammonium molybdate, ferric pyrophosphate or ferric citrate are added to the cell culture medium, the spent medium is first removed and then the cells are homogenized and blue colored anthocyanins extracted to reduce the amount of metal salts present in the extract.

VI. Procedure for Up-Scaling Blue-Anthocyanin Culture/Production/Purification

Plant cell suspensions have a number of characteristics that are different from those of microbial cultures and which can affect their growth in bioreactors.

Plant cells in culture are large (100 µm long), bound by a rigid cellulose-based wall and they often have a very large vacuole. Individual cells are rare, as cultures include mainly groups of cells or aggregates of 2 mm in diameter or above. Plant cells grow slowly (doubling times of 2-3 days) and consequently have a relatively low oxygen requirement.

Slow growth is one of the more important characteristics when considering bioreactor use for commercial applications. As a consequence of the slow growth, bioreactor runs can be as long as 3 weeks, which reduces the number of runs possible, overall productivity of the system and requires strict maintenance of sterility. One method of increasing productivity is to increase the level of biomass. This can be achieved is several ways such as starting with a higher inoculum density, reducing the lag phase at the start of the culture by using actively growing cells as inoculum instead of stationary phase cells or using media compositions that enable faster cell growth. Using 2% (weight/volume) sucrose, plant cell cultures normally achieve biomass levels of around 10 g/L (dry weight). With a water content of 80-90%, the maximum biomass can be 90-100 g/L. In practice, biomass levels of 30-60 g/L (dry weight) would appear possible (Scragg, A. H., 1992, *Current Opinion in Biotechnology* 3: 105-109). This is achieved not only by using nutrient rich media, but also appropriate bioreactor rheology conditions of aeration, agitation, gas mixing and so forth.

The high cell densities and the degree of aggregation may cause problems with both mixing and aeration, although the supply of oxygen may be less of a problem due to the low requirement. With a microbial culture, mixing at high biomass levels can be solved by increasing the impeller speed and power input. Plant cells, however, have been regarded as sensitive to shear stress due to their size, cell wall and large vacuole (Taticek et al., 1991, *Plant Cell* 24: 139-158). It was this shear sensitivity that encouraged the use of pneumatic reactors (also known as airlift bioreactors) which do not include any mechanical stirring arrangements for mixing. In addition to the use of pneumatic/airlift bioreactors, a number of bioreactor and impeller designs have been developed in order to produce good mixing with low shear stress. However, even at the relatively low aeration rate possible (0.1 vvm) pneumatic/airlift bioreactors may suffer from depletion of carbon dioxide and other components. Further, airlift bioreactors are not suitable for volumes above 100 L making them unsuitable for large scale commercial production.

Mixing high levels of biomass has been investigated using various impeller designs. Hooker et al. (1990, *Biotechnol. Bioeng.* 35: 296-304) have compared a standard flat-bladed impeller (1.5 cm height) with heights ranging between 5.1 cm and 14 cm. These were fitted in a 5 L Brunswick F5 bioreactor and a suspension culture of *Nicotiana tabacum* used as the test culture. The use of the largest (14 cm) flat-bladed impeller run at 150 RPM achieved the highest growth rate. A 'cell-lift' impeller that is supposed to generate lower shear rates than a Rushton turbine has been further modified by removal of the normal sparger from the Bio Flo II and replaced by direct sparging into the base of the impeller. This combination of cell-lift and airlift has been used to cultivate *T. rugosum*. By using perfusion-type culture—the continuous replacement of the medium without loss of cells—a maximum biomass level of 27.6 g/L (dry weight) was achieved with no problems of mixing (Kim D-L, Cho, G. H., Pedersen, H., and Chin, 1991, *Appl. Microbiol. Biotechnol.* 34: 726-729). Thus, it is clear that biomass levels of 30 g/L could be produced in such a system.

The large scale cultivation of plant cells has been restricted mainly to bioreactors of 100 L and below. There are reports, however, of the cultivation of plant cells in volumes of up to 75000 L. For instance, Ritterhaus et al. (1990, *International Association for Plant Tissue Culture Newsletter* 61: 2-10) describe the setting up of a cascade of bioreactors with volumes of 75, 750, 7500, 15 000 L for the production of immunologically active polysaccharides by *Echinacea purpurea*. Subsequently, cultures of *Rauwolfia serpentina* were grown to the 75 000 L scale. No real figures are given for the biomass levels or growth rates, although a value of 200 g/L (wet weight) is mentioned. Multiples of INTERMIG stirrers were used in these studies. These complex stirrers have the properties of low shear forces, good mixing, good dispersion of bubbles and low energy consumption. It is clear from this report that industrial scale growth of plant cells is possible and has been achieved.

In recent years there has been a shift away from capital-intensive stainless steel bioreactors to the use of disposable or single-use bioreactors. For example, flexible plastic containers supported by rigid containment made single-use bioreactors possible. Mixing in single-use bioreactors can pose design problems. Until recently, the only disposable option was the Wave-style rocking platform bioreactor, essentially a bag on a platform that oscillates back and forth to create waves in a solution contained within. The wave-style rocking platform bioreactor is useful up to the 100 L scale. Now there are other options that allow single-use bioreactors to scale up to 2000 L (Scott, C., 2007, *BioProcess International Supplement* 5: 44-51). Thus, it is possible to use such single-use bioreactors during the scale-up of the seed train (e.g., the scale up of cell culture from plate to production for each batch) while relying on the large tanks (e.g., stainless steel tanks) for the final stages of the production process.

In the present disclosure, it is contemplated that large-scale extraction of blue-pigmented anthocyanins can be accomplished by employing similar methods utilized by those of skill in the art to extract anthocyanins from fruits or vegetables. The general extraction procedure involves the crushing and homogenization of cells to disrupt the cell membranes and thereby cause the release of anthocyanins. In the case of cell cultures, this can be achieved by using high-shear blades for cell rupture in commercial scale homogenizers that can pump and process large volume of biomass. In an example, the homogenized cell mass can be filtered to remove the broken cell debris and separate the cell extract. This can be performed in various ways including filtration or centrifugation, just as with fruits or vegetables that are currently used for commercial production of anthocyanins. The broken cell mass can be extracted repeatedly with the desired solvents to thoroughly extract all the available anthocyanins from the cells. The extracts can then be pooled and further filtered to remove fine particles and then concentrated via evaporation or freeze drying, if desired. The concentrate can then be pasteurized and stored in the cold until further use. In an example, small, single use reactors can be used in the early stage of the seed train, (e.g., going from 1 L to 25 L) and then using the stainless steel tanks for scaling up to 10,000 L or more.

VII. Uses of the Blue-Anthocyanin Preparations

Anthocyanins are extensively used as natural color additives in many food products such as soft drinks, beverages and yogurts. However, the color range of these compounds is limited and dependent on pH. For example, in the acidic conditions of soft drinks and yogurts, anthocyanins are pink or red. Blue color is produced by anthocyanins only at alkaline pH and so cannot be achieved in soft drinks and yogurts. Prior to this disclosure, a stable blue shade could only be obtained by using synthetic colors. For example, there are two synthetic blue pigments approved for use as food color additives (FD&C Blue 1, EU Code E133 and FD&C Blue 2, EU Code E132). However, there has been an increasing consumer pressure for 'natural' products over the past 10 to 15 years. Thus, by the methods described herein it is possible to produce a stable blue colored anthocyanin that could potentially replace the synthetic blue pigments currently in use. The types of anthocyanins do not change following treatment, just the color generated (from red to blue) which allow blue anthocyanins to be present at an acidic pH (such as a pH between 1 and 5).

The following examples are provided to illustrate certain particular features and/or embodiments. These examples should not be construed to limit the invention to the particular features or embodiments described.

EXAMPLES

Example 1

Ammonium Molybdate Treatment of Callus

This example illustrates the ability of ammonium molybdate to change the color of anthocyanins from red to blue using red cabbage callus as an exemplary system.

Thirty seeds of Red cabbage "Ruby ball" (*Brassica oleracea*) were put into 50 mL tube and 3040 mL of 25% bleach containing 1 drop of Tween-20 per 100 mL of bleach solution was added to the tube. The tube was agitated on the Labquake shaker for 15 minutes. Seeds and bleach were poured through sterile tea strainer. The seeds were then rinsed three times with sterile water and plated on germination medium based on MS salts including MS vitamins (BO254 in Table 1), 30 g/L sucrose and 2.0 g/L Phytagel. The pH of the medium was adjusted to 5.8 before autoclaving for 15-20 minutes at 121° C., 1.25 kg/cm$^2$. Seeds were maintained at 23° C. with a sixteen hour white fluorescent light (60 µM) period and an eight hour dark photoperiod for three weeks. After three weeks, germinated seedlings were cut with a scalpel into three parts: cotyledon, hypocotyls and root and transferred by forceps onto callus induction media based on MS salts, MS vitamins, 30 g/L sucrose and Phytagel with various concentrations of hormones, 2,4-D, NAA and BA (See Table 1). After 2 to 3 weeks, calli were successfully induced and some subcultures eventually grew more prolifically than others.

TABLE 1

| | Media compositions of cabbage callus culture* | | | | | | | |
|---|---|---|---|---|---|---|---|---|
| | B0254 I | B0278 II | B0279 III | B0280 IV | B0281 V | B0282 VI | B0283 VII | B0462 VIII |
| MS Salts (Phytotech Catalog # M524) (g/L) | 4.33 | 4.33 | 4.33 | 4.33 | 4.33 | 4.33 | 4.33 | 4.33 |

TABLE 1-continued

Media compositions of cabbage callus culture*

| | B0254 I | B0278 II | B0279 III | B0280 IV | B0281 V | B0282 VI | B0283 VII | B0462 VIII |
|---|---|---|---|---|---|---|---|---|
| MS Vitamins 1000X Stock Solution (Phytotech Catalog # M533) (mL/L) | 1.0 | 1.0 | 1.0 | 1.0 | 1.0 | 1.0 | 1.0 | 1.0 |
| 2,4-D (mg/L) | | 1.0 | 1.0 | | | 1.0 | 1.0 | 1.0 |
| NAA (mg/L) | | | | 2.0 | 4.0 | 2.0 | 2.0 | 2.0 |
| BA (mg/L) | | | 0.1 | | 0.1 | | 0.1 | 0.1 |
| Sucrose (g/L) | 30.0 | 30.0 | 30.0 | 30.0 | 30.0 | 30.0 | 30.0 | 30.0 |
| Phytagel (g/L) | 2.0 | 2.0 | 2.0 | 2.0 | 2.0 | 2.0 | 2.0 | 2.5 |

*Premix salts and vitamins prepared and added as per manufacturer's instructions Liquid suspension cultures were initiated by adding calli to 25 mL of Gamborg's B5 or MS salts media (see Table 2) in 125 mL Erlenmeyer flasks containing various amounts of the hormones, Dicamba, benzyl adenine (BA), 2,4-D (2,4-dichlorophenoxyacetic acid), 6-γ,γ-Dimethylallylaminopurine (2iP), Gibberellic acid (GA) or Indole 3-Acetic Acid (IAA) with Nitsch & Nitsch or MS vitamins and 30 g/L sucrose. The pH of the media was adjusted to 5.6 before autoclaving at 1.25 kg/cm$^2$ pressure at 121° C. for 15-20 minutes. The cultures were incubated at 23° C. under 60 μM white fluorescent light and 60 Watt incandescent light (16 hours photo period/day). Liquid suspension cultures were maintained on an orbital shaker at 100-120 RPM under these lighting and temperature conditions with fresh media replacement every 7 to 14 days.

TABLE 2

Media compositions of cabbage suspension cultures*

| | BO463 I | BO464 II | BO465 III | BO466 IV | BO467 V | BO468 VI | BO469 VII | BO470 VIII | BO471 IX |
|---|---|---|---|---|---|---|---|---|---|
| MS Salts (Phytotech Catalog# M524) (g/L) | 4.33 | | | | | | | | |
| MS Vitamins 1000X Stock Solution (Phytotech Catalog # M533) (mL/L) | 1.0 | | | | | | | | |
| Gamborg B5 Salts (Phytotech Catalog # G768) (g/L) | | 3.08 | 3.08 | 3.08 | 3.08 | 3.08 | 3.08 | 3.08 | 3.08 |
| NN Vitamins 1000X Stock Solution (Phytotech Catalog # N608) (mL/L) | | 1.0 | 1.0 | 1.0 | 1.0 | 1.0 | 1.0 | 1.0 | 1.0 |
| 2,4-D (mg/L) | 1.0 | 1.0 | 2.0 | 2.0 | | | | | 2.0 |
| 2iP (mg/L) | | | | | 0.1 | | 0.1 | 0.1 | |
| Dicamba (mg/L) | | | | | | | 2.0 | 2.0 | |
| GA (mg/L) | | | | | | | | | 1.0 |
| IAA (mg/L) | | | | | | | | | 2.0 |
| NAA (mg/L) | 2.0 | 2.0 | | | | | | | |
| Picloram (mg/L) | | | | | 2.0 | 2.0 | | | |
| BA (mg/L) | 0.1 | 0.1 | 0.1 | | 0.1 | 0.1 | | 0.1 | |
| Sucrose (g/L) | 30.0 | 30.0 | 30.0 | 30.0 | 30.0 | 30.0 | 30.0 | 30.0 | 30.0 |

| | BO472 X | BO531 XI | BO532 XII | BO533 XIII | BO534 XIV | BO535 XV | BO536 XVI | BO537 XVII | BO538 XVIII |
|---|---|---|---|---|---|---|---|---|---|
| MS Salts (Phytotech Catalog# M524) (g/L) | | 4.33 | | | | | | | |
| MS Vitamins 1000X Stock Solution (Phytotech Catalog # M533) (mL/L) | | 1.0 | | | | | | | |
| Gamborg B5 Salts (Phytotech Catalog # G768) (g/L) | 3.08 | | 3.08 | 3.08 | 3.08 | 3.08 | 3.08 | 3.08 | 3.08 |
| NN Vitamins 1000X Stock Solution (Phytotech Catalog # N608) (mL/L) | 1.0 | | 1.0 | 1.0 | 1.0 | 1.0 | 1.0 | 1.0 | 1.0 |
| 2,4-D (mg/L) | 2.0 | 2.0 | 2.0 | 2.0 | 2.0 | 1.0 | | 0.5 | |
| 2iP (mg/L) | | | | | 0.04 | | 0.01 | | 0.05 |
| Dicamba (mg/L) | | | | | | | | 2.0 | 2.0 |
| GA (mg/L) | 1.0 | | | | | | | | |
| IAA (mg/L) | 2.0 | | | | | | | | |
| Kinetin (mg/L) | 0.1 | | | | | | | | |
| NAA (mg/L) | | | 2.0 | 2.0 | | | | | 1.0 |
| Picloram (mg/L) | | | | | | 2.0 | 2.0 | | |
| BA (mg/L) | | | 0.01 | 0.01 | 0.02 | | 0.01 | | 0.05 |
| Sucrose (g/L) | 30.0 | 30.0 | 30.0 | 30.0 | 30.0 | 30.0 | 30.0 | 30.0 | 30.0 |

TABLE 2-continued

Media compositions of cabbage suspension cultures*

| | BO539 XIX | BO560 XX | BO613 XXI | BO639 XXII |
|---|---|---|---|---|
| MS Salts (Phytotech Catalog# M524) (g/L) | | | | |
| MS Vitamins 1000X Stock Solution (Phytotech Catalog # M533) (mL/L) | | | | |
| Gamborg B5 Salts (Phytotech Catalog # G768) (g/L) | 3.08 | 3.08 | 3.08 | 3.08 |
| NN Vitamins 1000X Stock Solution (Phytotech Catalog # N608) (mL/L) | 1.0 | 1.0 | 1.0 | 1.0 |
| 2,4-D (mg/L) | 2.0 | 2.0 | 1.0 | 2.0 |
| 2iP (mg/L) | 0.05 | | | 0.005 |
| Dicamba (mg/L) | | | 2.0 | |
| GA (mg/L) | 1.0 | | | 1.0 |
| IAA (mg/L) | 2.0 | | | 2.0 |
| Kinetin (mg/L) | | | | |
| NAA (mg/L) | | 0.5 | | |
| Picloram (mg/L) | | | | |
| BA (mg/L) | | 0.01 | 0.025 | |
| Sucrose (g/L) | 30.0 | 30.0 | 30.0 | 30.0 |

*Premix salts and vitamins prepared and added as per manufacturer's instructions Nine-month old suspended cells were re-plated onto solid media plates to allow selection of cells showing callus formation with pigmented cells using two different media (BO591 and BO664, Table 3). For further maintenance, the re-plated cells were transferred onto BO591 or BO662 medium containing 30 mg/L ammonium molybdate to evaluate whether 30 mg/L ammonium molybdate induced or enhanced pigmentation.

TABLE 3

Solid media compositions for replating cabbage suspension cultures*

| | BO591 | BO664 | BO662 |
|---|---|---|---|
| Gamborg B5 Salts (Phytotech Catalog # G768) (g/L | 3.08 | 3.08 | 3.08 |
| NN Vitamins 1000X Stock Solution of Phytotech Catalog # N608 (mL/L) | 1.0 | 1.0 | 1.0 |
| Sucrose (g/L) | 30.0 | 30.0 | 30.0 |
| Dicamba (mg/L) | 2 | 2 | 2 |
| 2iP (mg/L) | 0.05 | | 0.05 |
| IAA (mg/L) | 2.0 | | 2.0 |
| GA (mg/L) | 1.0 | | 1.0 |
| 2,4-D (mg/L) | 2.0 | 2.0 | 2.0 |
| 4-Chlorophenylacetic acid (mg/L) | | 2.0 | |
| Ammonium Molybdate (mg/L) | | | 30.0 |
| Phytagel (g/L) | 2.5 | 2.5 | 2.5 |

*Premix salts and vitamins prepared and added as per manufacturer's instructions Re-plated cells showed purple pigmentation on both BO591 and BO664 media. Pigmented sectors were isolated under dissection microscopes and transferred onto the same Gamborg's B5 solid medium (BO591) supplemental ammonium molybdate added at 0, 1, 3, 9, 12, 15, 27, 30, 60, 90, 120 and 150 mg/L. Molybdenum caused easy detection of anthocyanins in cabbage re-plated cells by imparting a blue hue to the pigments. Before addition of ammonium molybdate, the cells showed a mixture of reddish and yellow hue pigments, while all the treatments with varying concentrations of molybdenum showed bluish pigments. All the replicates (20 plates per treatments) gave pigmented cells, but molybdenum did not affect the cell growth on solid medium at tested levels. The presence of molybdenum in the medium seemed to influence the production of pigmented cells in the re-plated cells. The re-plated cells on the medium with molybdenum had more pigmented areas compared to the cells on medium without molybdenum. The pigmentation pattern was consistent all through the testing period of 200 days. Lower levels (e.g., less than 9 mg/L) of molybdenum caused red or mix of red/blue pigmentation, while the higher level (e.g., above 9 mg/L) of molybdenum produced blue pigments. The callus on medium with more than 9 mg/L of molybdenum gave pigments with bluish hue and the levels between 30 and 120 mg/L were conducive for enhanced pigmentation of blue color. Sections of callus with various levels of molybdenum (0, 30, 60, 90, 120 mg/L) showed that the pigmentation was not restricted to the periphery of the callus mass, but was dispersed throughout the callus mass. This is a feature distinct from that of the intact seedlings where the concentration of pigments was mostly on the peripheral layers though the crystallized pigments were noticed in the cortical and vascular regions.

These studies indicate that ammonium molybdate can alter the color of anthocyanins in red cabbage callus.

Example 2

Ammonium Molybdate Treatment of Purple Carrot Suspension Cells

This example illustrates the ability of ammonium molybdate to change the color of anthocyanins from red to blue in suspension cultures of purple carrot cells.

Carrot (*Daucus carota*) suspended cells of cell line PC11H38 were grown in 125 mL Erlenmeyer flasks including using DC1151 Medium on a gyratory shaker at 100 RPM in white fluorescence light (16 hours light/8 hours dark) at 23° C. After 7 days, 10 mL of spent medium was removed and fresh medium was added into the cultures to bring the volume up to 40 mL working volume. At day 14, the same subculture was repeated. At day 21, the cultures were transferred to 250 mL Erlenmeyer flasks and fresh medium was added to bring the volume up to 80 mL. At day 28, the cultures were moved to UV-B light condition (16 hours UV-B/8 hours dark) at 23° C. after decanting some medium and adding the same volume of fresh medium. Exposure of cultures to UV-B light induced the production of anthocyanins that are red to purple in color.

These anthocyanin-producing cultures were used for further studies with ammonium molybdate.

Medium DC1151 Recipe:
MS Salts (Phytotech Catalog #M524): 4.3 g/L
2,4-D: 1.5 mg/L
Sucrose: 30.0 g/L
NN Vitamins (1000× Stock Solution of Phytotech Catalog #N608): 1.0 mL/L Fourteen-day old cultures from suspensions of carrot suspension cell line PC11H38 were used as inoculum to test the effect of molybdenum on pigment color. These cultures were added to fresh DC1151 Medium to make 40 mL suspensions with 25% packed cell volume (PCV). Three replicates at each treatment of 0 and 100 mg/L of ammonium molybdate added to the medium were used to test molybdenum effect on anthocyanin color change to bluish hue. After 14 days, when anthocyanins were extracted from the cells, the extracts from the cells treated with 100 mg/L ammonium molybdate were blue in color, while extracts from cells grown with no added ammonium molybdate were purple.

These studies indicate that ammonium molybdate can alter the color of anthocyanins in suspension cultures of carrot cells.

Example 3

Characterization of Anthocyanins Present in Callus and Suspension Cells

This example illustrates the types of anthocyanins present in plant tissue cultures, using red cabbage callus or carrot suspended cells as an exemplary system.

Anthocyanins were extracted from approximately 0.25±0.04 g fresh weight of cabbage calli or carrot suspended cells with 1.5 mL 50% (v/v) aqueous ethanol including 0.1% $H_2SO_4$ or with 1.5 mL 99.9% (v/v) methanol including 0.1% $H_2SO_4$. The cells were collected in a microcentrifuge tube (2.0 mL) and homogenized with a bead mill homogenizer for 1 minute. The homogenates were centrifuged in a clinical centrifuge at 4000 RPM for 4 minutes and only the supernatants were moved in another microcentrifuge tube.

This extract was tested for its absorbance at 520 nm and anthocyanin content was calculated using Beer's law ($A_{520\,nm}$×1000×MW of cyanidin glucoside)/(extinction coefficient).

The amounts and types of anthocyanins found in the extracts were determined by LC/MS and by UV absorbance. The extracts were filtered through 0.45 µM Millipore filters and 100 µl of the sample was injected to LC-MS analysis. A Symmetry C18 column (100×2.1 mm i.d., 3.5 µm) (Waters, Milford, Mass., USA) was used. LC analyses were performed using a Waters (Milford, Mass., USA) high pressure liquid chromatography (HPLC) system equipped with a CTC Analytics PAL autosampler (Leap Technologies, Carrboro, N.C., USA), Waters 626 pump with 600S Controller and a Waters 2996 photodiode-array detector (PDA) scanning from 190 to 780 nm. MassLynx™ was used for data analysis. Gradient elution was carried out with water-0.1% formic acid (solvent A) and acetonitrile-0.1% formic acid (solvent B) at a constant flow-rate of 0.3 mL min$^{-1}$. A linear gradient profile with the following proportions (v/v) of solvent B was applied (t (min), % B): (0, 7), (5, 15), (20, 75), (25, 100), (35, 100), (35.1, 7) (45, 7). The samples were monitored at 520 nm. A Waters QuattroMicro triple-quadrupole mass detector (Milford, Mass., USA) was used simultaneously to obtain the MS data. Full-scan data acquisition was performed, scanning from m/z 150 to 1200 in profile mode. Total anthocyanin concentration of an unknown extract could then be expressed as cyanidin-3,5-diglucoside equivalents by summing the peak areas at 520 nm and comparing to the standard curve.

As illustrated in FIGS. 1A-1D, liquid chromatography/mass spectrometry (LC/MS) analysis of the anthocyanin composition of cabbage callus cells showed that the red color was primarily the result of anthocyanins of mass 919, 937, 949 and 967. Collision induced dissociation of each of these four molecular ions revealed in each case a daughter ion with $M^+=287$, indicating that all four were cyanidin type anthocyanins (Cyanidin-3-(coumaroyl)-sophoroside-5-glucoside (MW=919), Cyanidin-3-(ferulyl)-sopho roside-5-glucoside (MW=949), Hydrocyanidin-3-(coumaroyl)-sophoroside-5-glucoside (MW=937), Hydrocyanidin-3-(ferulyl)-sophoroside-5-glucoside(MW=967)). Compared to their greenhouse-grown counterparts, the cultured cells contained a simpler mixture of anthocyanins consisting of only cyanidins with acylated trisaccharides at the 4 position.

The LC/PDA/MS analysis confirmed the pigmentation of red cabbage callus to be four anthocyanin compounds. These studies also confirm that the addition of molybdenum did not change the types of anthocyanins, though it did change the color of these anthocyanins from red to blue.

LC/MS analysis of the anthocyanin composition of carrot suspension cells showed that carrot cells of cell line PC11H38 contained three different glycosylated and acylated anthocyanins with molecular weights of 949, 919 and 889 (FIGS. 2A-2C). Based on these findings PC11H38 accumulates the three acylated anthocyanins Cyanidin-3-(coumaroyl)-xylosylglucosyl-galactoside (MW=889), Cyanidin-3-(ferulyl)-xylosylglucosyl-galactoside (MW=919) and Cyanidin-3-(synapyl)-xylosylglucosyl-galactoside (MW=949).

Example 4

Exposure to Metal Treatment for Generation of Blue Pigmentation

This example illustrates the use of metal ions to generate blue pigments in plant tissue cultures, using red cabbage or purple carrot callus as an exemplary system.

Cyanidin-type anthocyanin can also develop blue color by chelation of $Fe^{3+}$, $Mg^{2+}$ and $Ca^{2+}$. The chelation of $Fe^{3+}$ and $Mg^{2+}$ with 4'-keto-quinoidal base of anthocyanin apparently plays an important role for the blue color in protocyanin. Two $Ca^{2+}$ ions coordinate with flavones to form the components, which brings about co-pigmentation as well as stabilization of the molecule (Kosaku Takeda, 2006, *Proceedings of the Japan Academy, Series B*, 82(4): 142-154). Kumi et al. (2006, *Phytochemistry*, 67: 992-998) reproduced blue color by mixing anthocyanin and flavonol from *Meconopsis grandis* with metal ion components of $Fe^{3+}$, $Mg^{2+}$ and $Ca^{2+}$. Therefore, metal ions like $Fe^{3+}$, $Mg^{2+}$ and $Ca^{2+}$ can be used to produce blue pigments.

Generally, in vitro production of blue color with $Fe^{3+}$, $Mg^{2+}$, Mo, $Ca^{2+}$, $Al^{3+}$, $Mn^{2+}$, $Zn^{2+}$, $Ni^{2+}$, $Cu^{2+}$, $Co^{2+}$, $Na^+$ and $K^+$ salts which are mostly micro components in plant tissue culture media can be conducted with aliquots of sonicated suspensions of red or purple colored plant cells of cabbage and carrot at pH 3.0 and 4° C. By mixing the extracts with one of $Fe^{3+}$, $Mg^{2+}$, Mo, $Ca^{2+}$, $Al^{3+}$, $Mn^{2+}$, $Zn^{2+}$, $Ni^{2+}$, $Cu^{2+}$, $Co^{2+}$, $Na^+$ and $K^+$ salts or their combination at varying concentrations, the optimal conditions for blue color development can be identified. The stability of developed blue color with pH, temperature, hydrophilicity and pressure can also be determined. Effect of temperature on blue anthocyanin stability can be investigated by exposing blue anthocyanin to a range of temperature between −20° C. to 121° C. from a few minutes to up to 24 hours. After such treatments, UV-VIS spectra and circular dichroism spectra can be used to determine the changes to the anthocyanins by comparing the spectra before and after treatment. Similar studies can be performed to evaluate the effect of pH ranging from 1 to 9 and polarity index between 4.3 and 10.2. The optimized concentration and combination of blue color generating agents other than ammonium molybdate can be added into the suspension culture of anthocyanin producing cells for generating blue colored pigment producing cultures. For example, a specific ratio of anthocyanin and metal salts may be required to generate the blue color. This was described by Kondo et al. (1994, *Angew. Chem. Int. Ed. Engl.* 33: 978-979) who reported the reconstitution of protocyanin, a blue colored anthocyanin found in corn flowers, using the purified anthocyanin, the flavone glycoside, $Fe^{2+}$ and $Mg^{2+}$. Kondo et al. showed that the reconstituted pigment was blue and exhibited the same UV-VIS spectrum as the natural protocyanin extracted from corn flowers. The ratio of anthocyanin:flavone glycoside:Fe:Mg in the reconstituted pigment was found to be 6-8:6-8:1:1. That is equal amounts of the anthocyanin and flavone glycoside and equal amounts of the metal salts.

Example 5

In Vitro Studies with Carrot and Cabbage Anthocyanin Extracts and Suspension Cells This example illustrates the use of metal ions at varying concentrations to generate blue pigments in carrot and cabbage anthocyanin extracts and suspension cells.

Carrot suspension cultures and extracts were prepared as described in Example 2. In vitro studies were conducted using anthocyanins prepared from suspension cultures of carrot cell line PC11H38 and the final extract was concentrated to provide an extract containing 10 g/L anthocyanins.

The effect of ferric pyrophosphate ($Fe_4(P_2O_7)_3$), ferric citrate ($C_6H_5FeO_7$) and ferrous sulfate ($FeSO_4$) on generating blue-colored anthocyanins was evaluated. Ferric pyrophosphate is used to fortify infant cereals and chocolate drink powders, as it causes no adverse color or flavor changes to food. One gram of ferric pyrophosphate contains 11.8% of $Fe^{3+}$. The effect of ferric pyrophosphate on production of blue-colored anthocyanins was determined by dissolving 0.5 grams of ferric pyrophosphate in 100 mL of deionized water to make a 100 mM solution and its pH was adjusted to pH 4.0. This ferric pyrophosphate stock solution was mixed with 500 µl of purple carrot extract (anthocyanin concentration 10 g/L, pH 2.6) with various mass ratios between ferric pyrophosphate stock solution and anthocyanin extract. The ratios ranged from 0.0008:1 to 19:1. The treated extracts showed very bright blue color from 0.9:1 ratio. The pH of the mixed solution was 3.5. The pH was varied from 2.0 to 7.9 gradually by the addition of 0.1N HCl and 0.1N NaOH. The color was pale red in a pH region between 2 and 3. However, the color changed from pale red to blue in a pH of 3 to 5. In a pH of 5 to 7.9, the color was very strong blue. Studies performed with ferric citrate generated similar results to those observed with ferric pyrophosphate. In contrast, ferrous sulfate generated a different hue of blue color with a mass ratio of 0.8:1.

The effect of ammonium molybdate (($NH_4)_2MoO_4$) on generating blue-colored anthocyanins was also evaluated. One gram of ammonium molybdate (($NH_4)_2MoO_4$) contains 48.9% of molybdenum. 9.6 grams of ammonium molybdate was dissolved in 100 mL of deionized water to make a 100 mM solution. The pH of the 100 mM ammonium molybdate solution was adjusted to pH 4.0. Ammonium molybdate stock solution was mixed with 500 µl of purple carrot extract (anthocyanin concentration 10 g/L, pH 2.6) to yield various mass ratios between ammonium molybdate stock solution and anthocyanin extract. The ratios were 0.0015:1, 0.003:1, 0.008:1, 0.015:1, 0.03:1, 0.08:1, 0.15:1, 0.3:1 and 0.7:1. The treated extracts showed very bright blue color from 0.08:1 ratio. The pH of the mixed solution was 3.1. The pH of the mixed solution with 0.15:1 ratio was varied from 3.2 to 7.8 gradually by the addition of 0.1N NaOH. The color was very strong blue in all the pH region of 3.2-7.8.

$Ca^{2+}$, $Na^+$ and $Mg^+$ treatments were conducted in the same way as ferric pyrophosphate (above). Treatment of anthocyanin extracts with $Ca^{2+}$, $Na^+$ and $Mg^+$ did not produce blue anthocyanins even at high mass ratios.

*Brassica oleacea* suspended cells from cultivar Ruby Ball (cell line MX797-12) were cultured in 500 mL Erlenmeyer flasks including 120 mL DC1151 Medium (Recipe described in Example 2) on a gyratory shaker at 120 RPM in white fluorescence light (16 hours light/8 hours dark) at 23° C. After 7 days, the spent medium was removed and replaced with BO1224 Medium as production medium. At day 14, the cells were harvested and cabbage anthocyanins were extracted from the cells as described in Example 3 and the concentration of anthocyanins was adjusted to 10 g/L.

Recipe for Medium BO1224
Modified MS Basal Salts
(Phytotech Catalog #M531): 0.78 g/L
NN Vitamins (1000× Stock Solution of Phytotech Catalog #N608): 1.0 ml/L
2,4-D: 1.5 mg/L
Sucrose: 80.0 g/L The effect of ferric pyrophosphate ($Fe_4(P_2O_7)_3$), ferric citrate ($C_6H_5FeO_7$) and ferric ammonium citrate ($C_6H_{11}FeO_7$) for blue anthocyanin production with cabbage extracts was evaluated. Stock solutions of $Fe^{3+}$ were prepared by dissolving 4 grams of each ferric ion source chemical in 100 mL of deionized water to make 40,000 ppm solution. The pH of the solution was adjusted to pH 3.0 and solutions were filtered using Tissue Culture Filter Units (MF75 series, Nalgen, Rochester, N.Y.). These stock solutions were mixed with 0.5 mL of the cabbage anthocyanins extract (10 mg/mL) in the mass ratio of 2:1 ($Fe^{3+}$:anthocyanins). The pH of each of the mixed solutions was measured respectively, which were between 2 and 3. All treatments lead to a blue color as shown in Example 6 below.

These studies demonstrate the ability to generate blue anthocyanins by combining metal ions such as ferric citrate, ferric pyrophosphate and ammonium molybdate, with an anthocyanin extract at various ratios. These studies also demonstrate that $Ca^{2+}$, $Na^+$ and $Mg^+$ treatments conducted in the same way do not produce blue anthocyanins.

Example 6

Color Measurement using L*a*b* Color Space

This example illustrates the use of the L*a*b* color measurement scale (also referred to as CIELAB) for measuring color of extracts, such as determining the difference between untreated carrot extract and extract treated as described herein to produce blue pigments.

The L*a*b* color measurement scale (also referred to as CIELAB) is a well known method for measuring color and is widely used in various fields. In this space, L* indicates lightness and a* and b* are the chromaticity coordinates. FIG. 3 shows an a*, b* chromaticity diagram. In this diagram, a* and b* indicate color directions: +a* is the red direction, −a* is the green direction, +b* is the yellow direction, and −b* is the blue direction. The center is achromatic; as the a* and b* values increase and the point moves out from the center, the saturation of the color increases.

Color differences between untreated carrot extract and blue colored (treated) extracts were measured using a color spectrophotometer (UltraScan® VIS, Hunter Lab, Reston, Va.). Treatments with $Fe^{3+}$ and molybdenum shifted the color of carrot extract to lower a* (green) and lower b* (blue) values region in L*a*b* color space as shown in Table 4. These results demonstrate that $Fe^{3+}$ and molybdenum generated bluish color.

Similar measurements were made with cabbage anthocyanin extracts prepared as described in Example 5. For measurement of L*a*b* values of the mixed solution, they were diluted 10,000 times. Table 5 shows that the b* values of the mixed solution shifted down, which means $Fe^{3+}$ treatment changed the cabbage extracts color to more bluish color.

TABLE 4

Blue color formation in anthocyanin extracts from carrot cell suspension cultures treated with various metal salts.

| Treatment (mass ratio) | Color | L* | a* | b* |
|---|---|---|---|---|
| Untreated Carrot extract | Red | 49.48 | 69.98 | 35.09 |
| Carrot extract + $Fe^{2+}$ (1:1) | Light Blue | — | — | — |
| Carrot extract + $Fe^{3+}$ (1:1) | Blue | 17.81 | 45.43 | −1.81 |
| Carrot extract + Mo (1:1) | Dark Blue | 19.31 | 28.56 | −20.33 |
| Carrot extract + $Ca^{2+}$ (1:1) | Red | 48.92 | 65.34 | 32.57 |
| Carrot extract + $Mg^+$ (1:1) | Red | 49.23 | 66.92 | 35.79 |
| Carrot extract + $Fe^{2+}$ + Mo (1:1:1) | Green | — | — | — |
| Carrot extract + $Fe^{3+}$ + Mo (1:1:1) | Bluish green | 41.13 | 26.90 | −18.06 |
| Carrot extract + $Fe^{2+}$ + $Fe^{3+}$ (1:1:1) | Blue | — | — | — |
| Carrot extract + $Fe^{2+}$ + $Fe^{3+}$ + Mo (1:1:1:1) | Green | — | — | — |
| Carrot extract + $Fe^{3+}$ + $Ca^{2+}$ (1:1:1) | Dark Green | — | — | — |
| Carrot extract + $Fe^{3+}$ + $Mg^+$ (1:1:1) | Blue | — | — | — |

TABLE 5

Blue color formation in anthocyanin extracts from cabbage suspension cultures treated with Fe3+ ions.

| Sample | L* | a* | b* |
|---|---|---|---|
| Cabbage extracts (Untreated Control) | 39.5 ± 0.2 | 60.2 ± 0.1 | 46.4 ± 1.8 |
| Cabbage extracts + $Fe_4(P_2O_7)_3$ | 44.2 ± 0.1 | 55.1 ± 0.1 | 4.2 ± 0.1 |
| Cabbage extracts + $C_6H_5FeO_7$ | 42.6 ± 1.3 | 51.6 ± 1.1 | 0.9 ± 0.1 |
| Cabbage extracts + $C_6H_{11}FeO_7$ | 42.6 ± 0.1 | 53.3 ± 0.1 | 3.4 ± 0.2 |

Example 7

In Vivo Production of Blue-Colored Anthocyanins

This example illustrates the in vivo production of blue-colored anthocyanin from carrot or cabbage extracts.

In vivo production of blue-colored anthocyanin from carrot suspension cultures was tested as described below using a 1:1 mass ratio of $Fe^{3+}$/Mo and carrot anthocyanin. Two grams of ferric pyrophosphate was dissolved in 50 mL of fresh carrot suspension culture medium (pH 5.4). A 7 day-old culture from PC11H38 was used as inoculum to test the effect of ferric pyrophosphate on pigment color. For a one to one mass ratio between anthocyanin and $Fe^{3+}$, 4.4 mL of the solution was added to 40 mL of 7 day-old carrot suspension culture (anthocyanin productivity=1.0 g anthocyanin/L of culture) in 125 mL flask. The culture was incubated at 23° C. under UV-B light condition (16 hours light/8 hours dark, 280-320 nm) for four days. After four days, anthocyanins were extracted from the cells with acidified water (0.05% sulfuric acid, pH 3.0) as described in Example 3. The color of the extract was stable bluish purple under acidic (pH 3 to 4) condition. Its L*a*b* values (as described in detail in Example 7) were 56.2, 44.3 and −5.2 as measured using a color spectrophotometer (UltraScan® VIS, Hunter Lab, Reston, Va.).

Seven-day old suspension culture of *Brassica oleracea* Ruby Ball (MX797-12) was used for $Fe^{3+}$ treatments with three different source chemicals (ferric pyrophosphate, ferric citrate and ferric ammonium citrate). Appropriate amounts of each stock solution prepared as described in Example 5 were added to 40 mL of cabbage suspension cell culture in 125 mL Erlenmeyer flasks to provide a mass ratio of 1:1 (anthocyanins:$Fe^{3+}$). Each treatment had 3 replicates. The cultures were incubated at 23° C. under white fluorescence light condition (16 hours light/8 hours dark) for 7 days. After 7 days, anthocyanins were extracted from the cells with acidified water (0.05% sulfuric acid). The extracts from cells grown in the presence of $Fe^{3+}$ were more bluish in color as shown by the L*a*b* values in Table 6. L*a*b* measurements are described in detail in Example 8 below.

TABLE 6

L*a*b* values of cabbage anthocyanin extracts prepared from cells grown with or without $Fe^{3+}$.

| Treatment | L* | a* | b* |
|---|---|---|---|
| Control (No treatment) | 35.5 ± 0.1 | 60.4 ± 0.1 | 55.9 ± 0.9 |
| $Fe_4(P_2O_7)_3$ | 41.8 ± 0.2 | 51.9 ± 0.1 | 1.2 ± 0.3 |
| $C_6H_5FeO_7$ | 31.7 ± 0.3 | 39.0 ± 0.2 | 1.2 ± 0.3 |
| $C_6H_{11}FeO_7$ | 38.3 ± 0.3 | 28.7 ± 0.2 | 20.9 ± 0.1 |

Example 8

Spectrophotometric Evaluation of Color Changes in Blue-Colored Anthocyanins

This example illustrates the spectrophotometric evaluation of color changes of blue-colored anthocyanin by $Fe^{3+}$ in cabbage extracts.

Cabbage (*Brassica oleracea*) suspension cultures were raised as described in Example 1. From these established cabbage suspension cultures, 10 mL PCV of suspended cells were grown in 125 mL Erlenmeyer flasks including 30 mL of DC1151 Medium (Recipe in Example 2). The flasks were covered with silicon foam caps and agitated at 110 RPM with gyratory shaking in a thermostatically controlled room at 23±1° C. After 7 days of cell growth, the suspended cells were transferred to 30 mL of fresh medium for cell line maintenance and were thereafter subcultured weekly. Anthocyanin from seven day-old cultures of *Brassica oleracea* suspended cells was extracted by the extraction method described in Example 3 and its L*a*b* values were measured using a color spectrophotometer (Ultrascan® VIS, Hunter Lab, Reston, Va.) to compare color difference with other extracts.

Spectrophotometric analysis was conducted to compare $Fe^{3+}$-treated blue anthocyanin with other commercial products that are used as color additives. Generally, cabbage extracts show more bluish color than carrot extract. Therefore, commercial cabbage extracts from two different companies were analyzed. The commercial extracts were from Colarôme, Inc. (St-Hubert (Quebec) Canada) (Commercial cabbage extract A in Table 4) and from Diana Naturals (ANTRAIN, France) (Commercial cabbage extract B in Table 4).

Table 4 shows the L*a*b* values of various blue color anthocyanins made and compares them to commercial samples of cabbage anthocyanins. Each of the samples were normalized to a standard L* value of 57 by diluting each sample appropriately with acidic water, pH3.0. The a* value of carrot extract shifted down from 61.02 to 46.88, and the b* value also decreased from 6.23 to −4.34. It clearly shows $Fe^{3+}$ treatment changed red color of natural anthocyanin to blue color. $Fe^{3+}$-treated anthocyanins' b* value were closer to the values of commercial cabbage extracts. Additionally, the cabbage extracts made from cabbage suspension cultures and the carrot extracts made from carrot suspension cultures were combined in various ways at different ratios to test for blue color enhancement as well. Addition of any amount of blue anthocyanin extract to either cabbage extract or normal carrot extract made the combined extract bluer.

TABLE 7

Comparison of blue anthocyanin extract prepared from carrot cell extracts treated with metal salts with commercial anthocyanin extracts of red cabbage and anthocyanin extracts prepared from cabbage suspension cells.

| Sample Name | L* | A* | b* |
|---|---|---|---|
| Commercial cabbage extract A | 57.99 | 63.05 | −8.76 |
| Commercial cabbage extract B | 57.87 | 62.89 | −12.4 |
| cabbage suspension culture | 57.77 | 45.45 | 7.44 |
| carrot suspension culture | 57.37 | 61.02 | 6.23 |
| blue carrot extract | 57.82 | 46.88 | −4.34 |
| cabbage:blue carrot = 3:1 | 57.39 | 44.28 | 2.79 |
| cabbage:blue carrot = 1:1 | 57.56 | 42.85 | −0.27 |
| cabbage:blue carrot = 1:3 | 57.32 | 44.72 | −2.55 |
| carrot:blue carrot = 3:1 | 57.7 | 53.34 | −1.68 |
| carrot:blue carrot = 1:1 | 57.84 | 49.83 | −3.7 |
| carrot:blue carrot = 1:3 | 57.7 | 48.84 | −4.22 |

Example 9

Effect of Acidic Conditions on a Blue-Anthocyanin Solution

This example illustrates the ability of a blue anthocyanin solution to maintain a bluish hue even under acidic conditions.

Ten mL of various acids were added to 10 mL of a blue anthocyanin solution prepared from carrot suspension cultures as described in Example 7 with 1:1 volume ratio to test the possibility of color change back to red. 1N HCl, citric acid, acetic acid, and pH 3.0 buffer solution (VWR International, West Chester, Pa., USA) were chosen for this example. The anthocyanins solution showed a bluish hue consistently with all of the acid solutions. Further, 10 mL of commercial soda, SPRITE® which contains citric acid, was also mixed with the blue anthocyanin and the color of the resulting solution maintained its bluish hue.

Example 10

Generation of Uniformly Blue Pigmented Calli

This example illustrates the ability to generate uniformly blue pigmented calli by subculture of the blue pigmented areas generated from methods such as those described herein, including in Examples 1 through 4 and 7.

Cell cultures are typically callus or cell suspensions. Such cultures may be highly variable with respect to the cell types in the culture. Some of the variation may be generated from the culturing process but is also encouraged by the culture conditions used to maintain high growth rates. Cell lines may be a mix of undifferentiated cells and cells in the early phases of differentiation. Moreover, in cell suspensions a wide range of cell aggregate sizes occurs, and these can generate variation due to cell to cell communication within the larger aggregates. Such variation is most easily observed in cell lines producing pigments, such as the anthocyanins or carotenoids. This heterogeneity results in unbalanced cell growth and unstable production pattern in large-scale suspension culture. Cell selection process can provide suitable cell culture materials for efficient scale-up process. Many secondary metabolites are produced by cultures which are either not growing or are growing very slowly (Payne et al., 1992, "Plant Cell and Tissue Culture in Liquid Systems", pg 65). Therefore, the development of selective and rapid screens to detect target anthocyanin by pigment detection and cell growth is important for successful scale-up process. In cell cultures which are capable of synthesizing a visibly pigmented secondary metabolite the culture can be screened by eye and the high yielding cell clusters plated directly (Dix, 1990, "Plant Cell Line Selection"). Visible detection method of anthocyanin can be a high-throughput screening method utilized for identifying productive cell lines. For example, purple pigmented callus can be easily observed with naked eyes and collected. Ammonium molybdate will be added to the maintenance medium whereby blue pigmented callus is easily detected and subcultured. Blue pigmented callus from complex of anthocyanin and molybdenum can be selected with naked eyes and this will enable the selection of pigment-producing calli and enhanced total anthocyanin productivity.

These studies indicate that uniformly blue pigmented calli can be produced from red cabbage callus.

Example 11

Liquid Cultures of Uniformly Blue Pigmented Callus

This example illustrates the ability to generate uniformly blue pigmented suspension cultures by subculture of the uniformly blue pigmented calli generated from studies described in Examples 10.

In suspended cell culture, Packed Cell Volume (PCV, %) can be also deployed as a measuring method of biomass growth. PCV is the percentage by volume of packed plant cells in a given sample of cell culture (cell volume/total culture volume). Carbohydrate consumption rate measured by BRIX is also a very important factor for determining not only cell growth but also the cellular metabolic status. At each subculture stage care is taken to only transfer pigmented cells to the fresh medium. This is accomplished by pipetting mainly aggregates of pigmented cells during the transfer. This process is repeated several times until uniformly pigmented cell suspensions are derived by selectively subculturing only the pigmented cells. The entire resultant suspension is likely to be pigmented and a homogeneous suspension of pigmented cells established. These three parameters can be used for selecting well-producing and well-growing cells from heterogeneous cell cultures. Every two weeks, the measurement of anthocyanin productivity by visible detection method and PCV are being conducted and the best-performing cell cultures are collected based on these data.

Example 12

Up-Scaling the Production of Blue-Anthocyanin Compounds

This example illustrates methods that allow large scale production of blue anthocyanin pigments.

Two grams of ferric pyrophosphate was dissolved in 50 mL of carrot suspension culture medium (pH 5.4) and 7 day-old culture from PC11H38 was used as inoculum to test the effect of ferric pyrophosphate on pigment color. For 1:1 of mass ratio between anthocyanin and $Fe^{3+}$, 17.2 mL and 86 mL of the solution were added to 150 mL and 400 mL of 7 day-old carrot suspension culture (anthocyanin productivity=1.0 g anthocyanin/L of culture) in 500 mL and 1 L flasks respectively. In total the culture was incubated at 23° C. under UV-B light condition (16 hours light/8 hours dark, 280-320 nm) for 4 days. After 4 days, anthocyanins were extracted from the cells with acidified water (0.05% sulfuric acid, pH 3.0). The color of the extract was stable bluish purple under acidic condition and their L*a*b* values were measured using color spectrophotometer (UltraScan® VIS, Hunter Lab, Reston, Va.). L*a*b* values from 125, 500 and 1000 mL flask cultures were very similar and consistent, which was 57.4, 45.5 and −4.3. Final cell volume was 1.2 L of cells from 10×1 L flasks and 45 mL of 1% anthocyanin solution was achieved.

For commercial production of plant secondary metabolites, it is beneficial that improved strains be selected and optimal media developed as well. In an example, investigation aimed at improvement of cell growth and productivity is carried out on a flask scale and then the results of these investigations are implemented on a large scale. Plant secondary metabolite production has typically been induced by changing medium from a growth medium which usually is a nutrient rich medium to a production medium which usually is a nutrient limiting medium or contains chemical elicitors to induce stress on the cells to elicit production of secondary metabolites which permits slower growth and secondary metabolite production.

Production medium optimization is used to enhance production of anthocyanin. Factors that may be considered are dissolved oxygen (DO) level and micronutrient concentrations in the medium ($Mo^{6+}$, $Fe^{3+}$, $Ca^{2+}$ $Mg^{2+}$). For example, the gas composition and the gassing method can contribute to cell viability and useful production. There may also be interactions between dissolved gas and anthocyanin concentration. Additionally, ferric ions can contribute to blue color development and chelate orthodihydroxy group of the B-ring of the anthocyanin nucleus. Moreover, magnesium concentration can alter plant anthocyanin concentrations and such concentrations may be furthered influenced by temperature (e.g., elevated temperature regimes enhance the magnesium-induced increases in plant anthocyanin concentrations).

Thus, in the production of blue colored anthocyanins from cell culture the cells are initially scaled up to the desired production volume in a medium optimized for rapid cell growth. Once the cell culture density has reached the desired biomass level for production and the cells have produced normal colored anthocyanins (such as, red or purple), the spent medium is removed and replaced with fresh production medium containing the desired amount of blue pigment producing agent, such as 100 mg/L ammonium molybdate. The cultures are allowed to grow for an additional period of time (such as 24 hours) and harvested to extract blue colored anthocyanins.

While this disclosure has been described with an emphasis upon particular embodiments, it will be obvious to those of ordinary skill in the art that variations of the particular embodiments may be used and it is intended that the disclosure may be practiced otherwise than as specifically described herein.

Accordingly, this disclosure includes all modifications encompassed within the spirit and scope of the disclosure as defined by the following claims:

1. A method for producing blue anthocyanin pigments, comprising:
   providing a plant callus from a plant that produces anthocyanin;
   cultivating the plant callus in a liquid medium to obtain a suspension cell culture comprising callus cells producing blue anthocyanin, wherein the liquid medium comprises a blue anthocyanin-generating agent at a concentration sufficient to obtain the suspension cell culture producing blue anthocyanin pigments that maintain a bluish hue under acidic conditions at a pH of 3.2; and
   recovering the blue anthocyanin pigments from the suspension cell culture.

2. The method of claim 1, wherein providing the plant callus comprises inducing the formation of the plant callus from a tissue explant of a plant capable of producing blue anthocyanin through in vitro culture in a suitable nutrient medium.

3. The method of claim 2, wherein the nutrient medium used in the induction step of the formation of the plant callus comprises a solid medium.

4. A method for producing blue anthocyanin pigments, comprising:
   providing a plant callus from a plant that produces red or purple anthocyanin;
   cultivating the plant callus in a liquid medium to obtain a suspension cell culture comprising callus cells producing blue anthocyanin pigments, wherein the liquid medium comprises a blue anthocyanin-generating agent at a concentration sufficient to generate callus with blue anthocyanin pigments that maintain a bluish hue under acidic conditions at a pH of 3.2; and
   recovering the blue anthocyanin pigments from the suspension cell culture.

5. The method of claim 4, wherein providing the plant callus comprises inducing the formation of the plant callus from a tissue explant of a plant capable of producing at least one of red or purple anthocyanin through in vitro culture in a suitable nutrient medium.

6. The method of claim 5, wherein the nutrient medium used in the induction step of the formation of the plant callus comprises a solid medium.

7. The method of claim 1, wherein the blue anthocyanin-generating agent comprises at least one of ammonium molybdate, a $Fe^{3+}$ salt, ferric pyrophosphate, ferric citrate, an $Al^{3+}$ salt, a $Mn^{2+}$ salt, a $Zn^{2+}$ salt, a $Ni^{2+}$ salt, a $Cu^{2+}$ salt, a $Co^{2+}$ salt, a $K^+$ salt, or a combination of two or more thereof.

8. The method of claim 7, wherein the blue anthocyanin-generating agent comprises ammonium molybdate.

9. The method of claim 8, wherein the concentration of ammonium molybdate is of 9 mg/L to 150 mg/L.

10. The method of claim 7, wherein the blue anthocyanin-generating agent comprises a $Fe^{3+}$ salt, ferric pyrophosphate, ferric citrate or combination thereof.

11. The method of claim 7, wherein the blue anthocyanin-generating agent comprises ammonium molybdate, ferric pyrophosphate, ferric citrate or a combination thereof.

12. The method of claim 10, wherein the blue anthocyanin-generating agent comprises ferric pyrophosphate, ferric citrate or a combination thereof.

13. The method of claim 4, wherein the blue anthocyanin-generating agent comprises ammonium molydate, ferric pyrophosphate, ferric citrate or a combination thereof.

14. The method of claim 1, wherein the plant is of the genus *Brassica*.

15. The method of claim 14, wherein the plant belongs to the species *Brassica oleraceae*.

16. The method of claim 1, wherein the plant is of the genus *Daucus*.

17. The method of claim 16, wherein the plant of the genus *Daucus* belongs to the species *Daucus carota*.

18. The method of clam 1, wherein the blue anthocyanin pigments are present at a pH of 1 to 5.

19. The method of claim 1, wherein the callus is obtained from a cotyledon, root, hypocotyl, shoot tip, stem, leaf, or epidermal peel.

* * * * *